US 6,740,499 B2

(12) United States Patent
Sethi et al.

(10) Patent No.: US 6,740,499 B2
(45) Date of Patent: May 25, 2004

(54) METHOD FOR DETECTING BACTERIAL EXACERBATIONS OF CHRONIC LUNG DISEASE

(75) Inventors: Sanjay Sethi, East Amherst, NY (US); Timothy F. Murphy, East Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 89 days.

(21) Appl. No.: 09/780,503

(22) Filed: Feb. 9, 2001

(65) Prior Publication Data

US 2002/0001820 A1 Jan. 3, 2002

Related U.S. Application Data

(60) Provisional application No. 60/181,620, filed on Feb. 10, 2000.

(51) Int. Cl.[7] .............................. C12Q 1/37; C12Q 1/00; C12Q 1/02; C12Q 1/68

(52) U.S. Cl. ............................... 435/24; 435/4; 435/29; 435/34; 435/6

(58) Field of Search .................. 435/24, 4, 29, 435/34

(56) References Cited

U.S. PATENT DOCUMENTS 5,686,070 A  * 11/1997  Doerschuk et al. ...... 424/145.1

OTHER PUBLICATIONS

Matsumoto, K; Verhandelingen–Koninklijke Academie voor Geneeskunde van Belgie [Verh K Acad Geneeskd Belg] 1995; V 57(2), pp. 109–122, (Abstract Only).*

Mikami, M; Nihon Kyobu Shikkan Gakkai zasshi[Nihon Kyobu Shikkan Gakkai Zasshi] 1991 Jan.; V. 29(1), pp. 72–83, (Abstract Only).*

Tsang et al, Chest, V117/2, pp. 420–426 (Feb., 2000).*

Burrows, et al, Course and Prognosis of Chronic Obstructive Lung Disease, 1969, N. Engl. J. Med., vol. 280, pp. 397–404.

Sethi, Management of Acute Exacerbations of Chronic Bronchitis, 1998, Infect. Dis. Clin, Pract., 1998, 7:S300–S308.

Tager, et al., Role of Infection in Chronic Bronchitis, 1975, N. Engl. J. Med., vol. 292, No. 11, pp. 563–571.

Murphy et al., Bacterial Infection in Chronic Obstructive Pulmonary Disease, 1992, Am. Rev. Respir. Dis., 146:1067–1083.

Isada, Pro: Antibiotics for Chronic Bronchitis With Exacerbations, 1993, Seminars in Respiratory Infections, vol. 8, No. 4, pp. 243–253.

Nicotra et al., Con: Antibiotic Use in Exacerbations of Chronic Bronchitis, 1993, Seminars in Respiratory Infections, vol. 8, No. 4, pp. 254–258.

Pevnitsky, et al. Immunological Monitoring of Patients with Cystic Fibrosis: Value of Different Laboratory Findings. Vestnik Rossiiskoi Akademii Meditsinskikh Nauk, 2000, vol. 5, pp. 40–46, see English Abstract p. 46.

Elborn, et al. Host Inflammatory Responses to First Isolation of Pseudomonas Aerugonoisa from Sputum in Cystic Fibrosis. Pediatric Pulmonology. 1993, vol. 15, pp. 287–291, see entire document.

(List continued on next page.)

Primary Examiner—Louise N. Leary
(74) Attorney, Agent, or Firm—Hodgson Russ LLP (57) ABSTRACT

The present invention provides a method for distinguishing bacterial from non-bacterial exacerbations of chronic lung disease. The method comprises detecting the presence of elastase in patient sputum containing secretions of the lower respiratory tract.

19 Claims, 6 Drawing Sheets

OTHER PUBLICATIONS

Kudo, et al. Activity and Inhibitors in Sputum from Chronic Respiratory Diseases. Therapeutic Research. 1988, vol. 8, No. 2, pp. 526–533, see English Abstract on p. 533.

Kudo, Y. Elastolytic Activity and Inhibitors in Sputum from Chronic Respiratory Diseases. Tokyo Joshi Ika Daigaku Zasshi. 1991, vol. 61, No. 2, pp. 124–132, see English Abstract on p. 124.

Crooks, et al. Bronchial Inflammation in Acute Bacterial Exacerbations of Chronic Bronchitis: The Role of Leukotriene $B_4$. Eur. Respir. J. 2000, vol. 15, pp. 274–280, see entire document.

Tsang, et al. Sputum Elastase in Steady–State Bronchiectasis. Chest. Feb. 2000, vol. 117, pp. 420–426, see entire document.

Hill, et al. The Interrelationship of Sputum Inflammatory Markers in Patients with Chronic Bronchitis. Am. J. Respir. Crit. Care. Med. 1999, vol. 160, pp. 893–898, see entire document.

Pukhalsky, et al. Inflammatory Markers in Cystic Fibrosis Patients with Lung Pseudomonas Aeruginosa Infection. Mediators of Inflammation. 1999, vol. 8, pp. 159–167, see entire document.

Sethi et al, *Comparison of Airway Inflammation in Acute Bacterial and Non–Bacterial Exacerbations of COPD*, American Journal of Respiratory and Critical Care Medicine, Mar. 1999, vol. 159, No. 3.

* cited by examiner

METHOD FOR DETECTING BACTERIAL EXACERBATIONS OF CHRONIC LUNG DISEASE

This application claims the priority of U.S. provisional application Serial No. 60/181,620 filed on Feb. 10, 2000, the disclosure of which is incorporated herein by reference.

FIELD OF THE INVENTION

The present invention relates generally to the area of lower respiratory tract infections. More particularly, the present invention provides a method for differentiating bacterial versus non-bacterial exacerbations of chronic lung disease.

DISCUSSION OF RELATED ART

Chronic bronchitis and other lung diseases including cystic fibrosis and bronchiectasis, are associated with intermittent exacerbations (such as acute exacerbations of chronic bronchitis (AECB)) that lead to worsening of the chronic symptoms of productive cough and dyspnea. These exacerbations cause considerable morbidity, and in patients with concomitant airway obstruction such as chronic obstructive pulmonary disease (COPD), are a major cause of mortality (Burrows et al., 1969, N. Engl. J. Med., 280:397–404). AECB can have one or more of several different etiologies (Sethi, 1998, Infect. Dis. Clin. Pract., 7:S300–S308). Virus infection, identified by a four-fold rise in antibody titer or by viral isolation, causes a third of exacerbations (Gump et al., 1976, Am. Rev. Respir. Dis., 113:465–473; Buscho et al., 1978, J. Infect. Dis., 137:377–383; Smith et al., 1980, Am. Rev. Respir. Dis., 121:225–232). Serological evidence of atypical bacterial infection, mostly by Chlamydia pneumoniae, is seen in 5–10% of exacerbations (Blasi et al., 1993, Eur. Respir. J., 6:19–22; Miyashita et al., 1998, Chest, 114:969–971). Bacterial pathogens, especially nontypeable Haemophilus influenzae, Streptococcus pneumoniae, Moraxella (Branhamella) catarrhalis and Pseudomonas aeruginosa are isolated from sputum in about 50% of exacerbations (Sethi, 1998, supra).

The role of bacterial pathogens as a cause of AECB is controversial for several reasons. Bacterial pathogens can be isolated from sputum during stable chronic bronchitis at the same frequency as during exacerbations. Serological studies examining antibodies to common bacterial pathogens and placebo-controlled antibiotic trials in AECB have yielded confusing and contradictory results. Though alternative explanations exist for these observations, many authors have interpreted them to show that bacterial pathogens play no role in AECB (Tager et al., 1975, N. Engl. J. Med. 292:563–571; Murphy et al., 1992, Am. Rev. Respir. Dis. 146:1067–1083; Isada, 1993, Antibiotics for chronic bronchitis with exacerbations. Seminars in Respiratory Infections. 8:243–253; Nicotra et al., 1993, Antibiotic use in exacerbations of chronic bronchitis. Seminars in Respiratory Infections. 8:254–258). This view holds that isolation of bacteria during AECB represents chronic colonization and is a mere epiphenomenon.

The absence of a more definitive and quick indication regarding the involvement of bacterial induced exacerbation of chronic lung disease makes the choice of treatment options difficult. Culturing of sputum to identify bacterial involvement is time consuming. Thus, there is an ongoing need for identifying markers that provide a simple and quick test to distinguish between different etiological causes of exacerbations of chronic lung disease, in particular to distinguish between bacterial and non-bacterial induced exacerbations.

SUMMARY OF THE INVENTION

The present invention provides a simple and quick test for discriminating between bacterial and non-bacterial exacerbations of chronic lung disease. The test is based on the unexpected observation of a strong correlation between bacterial AECB and sputum elastase. Thus, the test comprises obtaining a sputum sample from an individual such that it contains secretions of the lower respiratory tract, and testing it for the presence of elastase. For certain pathogens, a correlation is also observed between AECB and sputum IL-8 or TNF-α. Thus, in another embodiment, the levels of IL-8 or TNF-α may be tested. The amount of these markers is then compared to standard reference. The comparison may be done using a calorimeter or by visual means.

BRIEF DESCRIPTION OF THE DRAWINGS

FIG. 2A), Tumor Necrosis Factor α (TNF-α; FIG. 2B) and Neutrophil Elastase (NE; FIG. 2C).

FIG. 3A), Tumor necrosis factor α (TNFα; FIG. 3B) and Neutrophil elastase (NE; FIG. 3C).

DETAILED DESCRIPTION OF THE INVENTION

This invention provides a method for discriminating between bacterial and non-bacterial induced exacerbations of chronic lung disease. The term "chronic lung disease" as used herein includes, but is not limited to, chronic bronchitis, cystic fibrosis and bronchiectasis. Exacerbations of chronic lung disease are characterized by a worsening of symptoms of underlying lung disease characterized by increased shortness of breath, increased sputum production and increased sputum purulence compared to baseline symptoms. The present method is based on the unexpected observation that elastase levels are elevated during bacterial-induced exacerbations. For certain pathogens, a correlation was also observed between AECB and sputum IL-8 or TNF-α.

The method of the present invention comprises determining the presence or level of elastase in sputum that contains the secretions of the lower respiratory tract. In another embodiment, the method comprises determining the presence or level of IL-8 or TNF-α in the sputum samples. Sputum can be collected in a variety of ways, including expectorating into a cup, suctioning, induction with nebulized saline and bronchoalveolar lavage through a bronchoscope. In one embodiment, the sputum is induced with hypertonic saline solution. Suitable saline concentrations are in the range of 3 to 5 percent. An example of a suitable saline concentration is 2%. This is a well accepted method of inducing sputum that contains the secretions of the lower respiratory tract. For induction of sputum, a commercially available nebulizer may be used. Generally a volume of 10–30 mls is obtained.

A suitable volume of nebulized saline (such as 20 mls) is inhaled by the patient and then the patient attempts to expectorate serum till a sufficient amount is collected. For example, nebilized saline may be inhaled over a 20 minute period and the patient may attempt to expectorate sputum every 5 minutes.

Once a sufficient amount of sputum for analysis is obtained, it may be directly used for the determination of elastase, IL-8 or TNF-α. The sputum may also be processed for removal of cellular components such as by centrifugation or filtration. The supernatant may be assayed directly or stored frozen for future testing.

An aliquot of the sputum may be checked for the presence of lower respiratory tract secretions. Indicators for lower respiratory tract secretions include the presence of neutrophils (such as by gram staining) or the presence of fibrinogen. Fibrinogen is typically absent from the saliva and is taken as an indicator of lower respiratory tract secretions.

Elastase activity may be determined by any standard technique. One example is the use of a double antibody sandwich assay (such as described by Crooks et al., 1995, *J. Clin Microbiol.*, 33:924–929). Another example is the use of fluorogenic substrates as described in U.S. Pat. No. 4,336, 186. Chromogenic substrates that can be used include, but are not limited to, methoxysuccinyl-L-alanyl-L-alanyl-L-prolyl-L-valine 7 amino-4-methyl-coumarin (Shah et al., 1996, *Euro. Respir. J.*, 9:531–534; succinyl-L-alanyl-L-alanine-p-nitroanilide (Tsang et al., 2000, *Chest*, 117:420–426. One method involves the use of a synthetic substrate N-methoxysuccinyl-ala-ala-pro-val p-nitroanilide (Fujita et al., 1990, *Am. Rev. Respir. Dis.*, 142:57–62). Reaction of elastase with this substrate produces a colored product detected at 405 to 570 nm. Quantitative determination can be made by comparison with a standard curve or a semi-quantitative determination can be made by comparing to a reference standard. Those skilled in the art will recognize that the reference standard may be a control sample run in parallel or a color graded reference strip.

For use in a semi-quantitative manner, the elastase assay may be carried out as a dipstick or test strip assay. The test strip or dipstick has an absorbant carrier such as a filter paper, felt, porous ceramic strips and glass fiber materials. The test strip or dipstick is impregnated with the substrate in a suitable buffer system. The test strip can be directly dipped into the test sample. A semi-quantitative estimate may be made by comparing to a color graded chart or comparing to a reference standard.

For quantitative determination, the sputum sample may be optionally diluted. The sample is then allowed to contact its chromogenic or fluorogenic substrate. Any elastase activity present in the sample will cause a change in the emission spectrum of the substrate such that it may be detected using a standard calorimeter. A parallel set of standards may be used to determine the level.

Determination of IL-8 and TNF-α levels can be carried out by standard techniques such as by ELISA assays using commercially available reagents.

These and other applications will become more clear from the following examples, which are intended to be illustrative and not restrictive. While the examples given below refer to AECB, those skilled in the art will recognize that the test may be equally applicable to other infections of the lower or upper respiratory tract.

EXAMPLE 1

This embodiment describes the collection of sputum samples during bacterial exacerbations of chronic lung disease.

A total of 74 patients were enrolled in a prospective, longitudinal study of the dynamics and immune response to bacterial infection in chronic bronchitis from March 1994 to December 1997. Inclusion criteria were a) presence of chronic bronchitis as defined by the American Thoracic Society (1995, *Am. J., Respir. Crit. Care Med.*, 152:S77–S120; b) absence of asthma or bronchiectasis by clinical assessment; c) ability to comply with monthly clinic visits; d) absence of immunosuppression (<20 mg/day prednisone was allowed) or other life-threatening illness. The subjects were seen monthly, and whenever they were experiencing symptoms suggestive of an AECB, in an outpatient study clinic at the Buffalo Va. Medical Center.

At each visit, clinical information, sputum and serum samples were collected. Of a total of 1503 clinic visits, the subject's COPD was clinically stable in 1227 (81.6%) of these visits, while in 276 (17.4%) visits, the subject was experiencing an AECB. Whether a patient was stable or experiencing an exacerbation was determined as follows. At each visit, the subject was questioned about the status of his chronic respiratory symptoms, and the responses were graded as 1) same as baseline 2) somewhat worse than baseline or 3) much worse than baseline. If there was minor worsening of 2 or more symptoms or a major worsening of 1 or more symptoms, a clinical assessment was made as to the cause. If necessary, a chest x-ray was obtained. If no other cause, such as pneumonia, upper respiratory infection, congestive heart failure was identified, the patient was determined to be experiencing an exacerbation.

An overall clinical score was calculated at each visit, which served as a measure of clinical severity of the AECB episode. At each clinic visit in the longitudinal study, ten clinical parameters (overall well being; dyspnea; cough; sputum production, viscosity, and purulence; overall appearance, respiratory rate, wheezing and rales) were assessed and graded from 1 to 3 as described above. A score of 10 represented baseline and a score of 30 represented the sickest patient.

Figure 1:
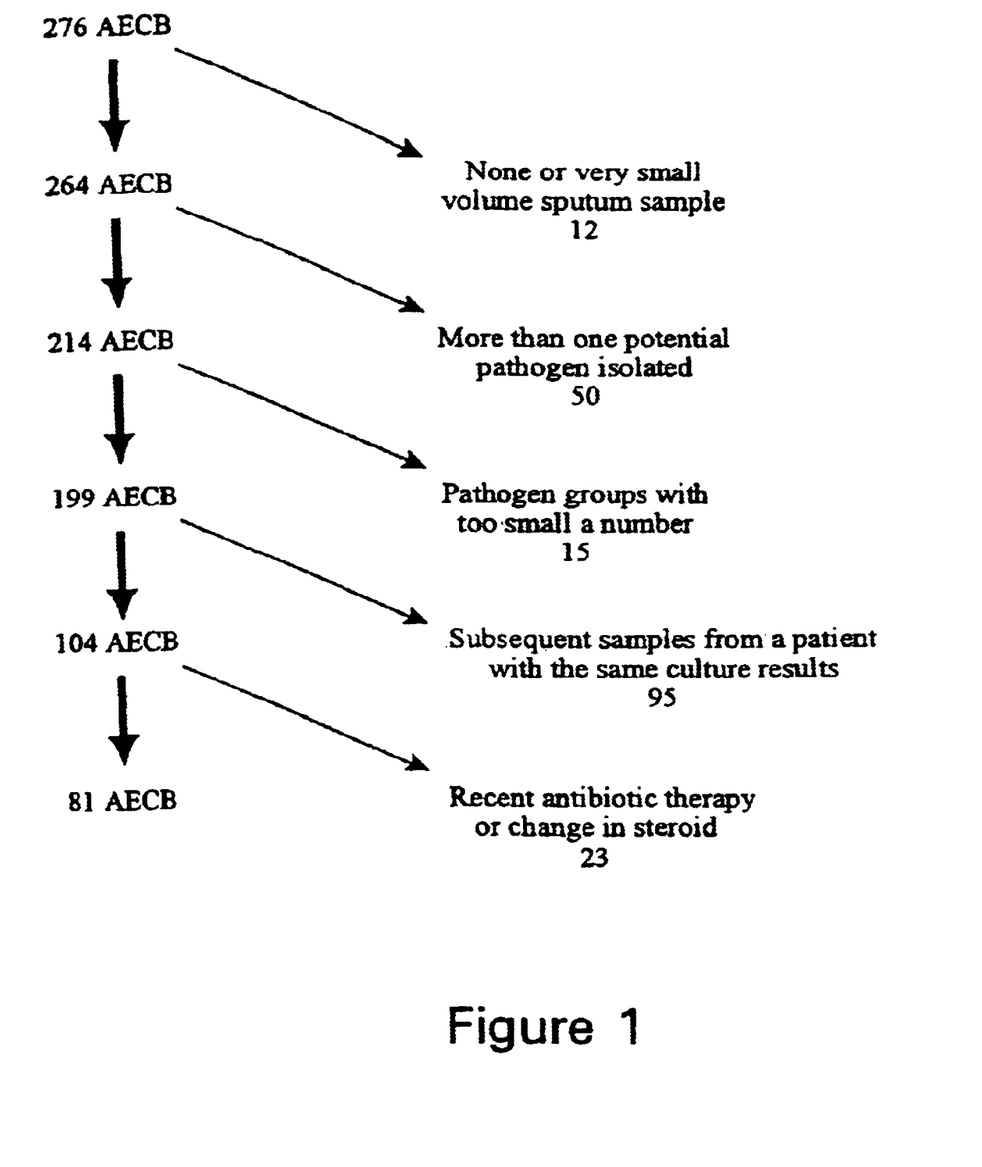
FIG. 1 is a representation of sputum sample selection flow sheet for data generated in Example 1.

Sputa collected were spontaneous morning samples. The whole sputum sample was weighed, graded macroscopically for purulence and viscosity, and homogenized by incubation at 37° C. for 15 min. with an equal volume of 0.1% dithiothreitol (Sputolysin, Calbiochem). Serial dilutions of homogenized sputum were prepared in phosphate buffered saline (PBS) and plated on blood, chocolate and MacConkey agar plates. Bacterial identification was performed by standard techniques. If *H. influenzae*, *M. catarrhalis* or *S. pneumoniae* were present, an attempt was made to isolate and characterize 10 individual colonies of each bacterial species. Bacterial titers were measured by counting the number of colonies in the dilution plates and multiplying the count by the appropriate dilution factor. The remainder of the sputum sample was centrifuged at 25,000 g for 45 minutes at 4° C. and the resultant supernatant was stored at −70° C. Of the 276 episodes of AECB, sputum supernatant obtained in 81 exacerbations in 45 patients was selected to be included in this study as shown in FIG. 1. These selection criteria allowed the avoidance or overrepresentation by patients who had frequent exacerbations.

As shown in Table 1, the population was predominantly an elderly male population. On enrollment, 26 (58%) of the subjects had severe ($FEV_1$<50% predicted), 12 (27%) had moderate ($FEV_1$50–64% predicted), 2 (4%) had mild ($FEV_1$65–80% predicted) COPD and 5 (11%) had chronic bronchitis only.

TABLE 1

Demographic characteristics of patients whose sputum samples were included in this study.

| | |
|---|---|
| Mean age (range) | 65.4 (46–82) |
| Sex (n) | Male: 44 |
| | Female: 1 |
| Race (n) | Caucasian: 36 |
| | African-American: 9 |
| Mean years since diagnosis of COPD (range) | 14.96 (2–58) |
| Smoking status on enrollment (n) | Ex-smokers: 26 |
| | Current smokers: 19 |
| Mean smoking pack-years (range) | 92.07 (10–185) |
| Mean $FEV_1$ in liters (range) | 1.68 (0.59–3.93) |
| Mean $FEV_1$ % predicted (range) | 49.07 (17–99) |

The sputum samples obtained during AECB were further classified as follows. Pathogen-negative AECB were those in which only normal flora was isolated from sputum obtained at the time of diagnosis. Normal flora was defined as the absence of the following pathogens in sputum: Haemophilus spp., *M. catarrhalis, S. pneumoniae, Staphylococcus aureus*, Psedomonas spp., and Gram-negative bacilii. Bacterial ACEB were those in which any of these pathogens were isolated from sputum culture. The bacterial AECB cases included in the present study were those from which *H. influenzae* or *M. catarrhalis* was the sole pathogen isolated from sputum obtained at the time of diagnosis. To examine the role of *Haemophilus parainfluenzae* as a pathogen in AECB, a group of exacerbations in which *H. parainfluenzae* was the sole 'pathogen' isolated, were also included. Neutrophilic inflammation was measured by quantifying interleukin-8 (IL-8), tumor necrosis factor alpha (TNF-α), and neutrophil elastase (NE) in the sputum supernatants. Pathogen-positive sputum samples were compared with pathogen-negative samples.

EXAMPLE 2

This embodiment describes the properties of sputum samples obtained from individuals in Example 1. As discussed above, sputum induction with hypertonic saline has become a widely accepted research technique to obtain lower respiratory tract secretions in airway diseases such as asthma and COPD. To assess the adequacy of the expectorated sputum samples as representative of the lower airway milieu, 52 consecutive induced sputum samples from 31 patients were compared with spontaneously expectorated sputum collected by the patient on the morning of the induction. A volume of 30 cc of hypertonic (3%) saline was nebulized over 15–20 minutes with an ultrasonic nebulizer (DeVilbiss) 099HD to induce sputum production. The paired (induced versus spontaneously expectorated) sputum samples were graded for purulence and viscosity, subjected to gram staining and microscopic examination and measurement of fibrinogen level (a marker for lower respiratory tract secretions). Table 2 shows the scoring system used to categorize the gross and microscopic features of the sputum specimens. These results indicate that induced and expectorated sputum are similar in the properties tested and therefore, either sputum may be used for the present invention.

TABLE 2

Scoring system for comparison of induced and spontaneous samples

| Characteristic | Score = 1 | Score = 2 | Score = 3 |
|---|---|---|---|
| Purulence | Mucoid | Mucopurulent | Purulent |
| Viscosity | Thin, watery | Thick | Extremely thick |
| Non-squamous cells | <10/lpf* | 10–25/lpf | >25/lpf |
| Squamous cells | <10/lpf | 10–25/lpf | >25/lpf |

*Low power field (10x) of microscope

Fibrinogen is absent in saliva and is present in measurable amounts in lower respiratory tract secretions. To assess the quality of the expectorated sputum samples, paired induced and expectorated sputa were subject to measurement of fibrinogen levels by using a competitive enzyme linked immunosorbent assay (ELISA; Fahy et al., 1993, *Am. Rev. Respir. Dis.* 147:1126–1131). For the samples tested in this example, the minimum fibrinogen level detectable was 30 ng/ml and the linear range of this assay was 60 ng/ml to 2000 ng/ml.

The only significant differences between the induced and expectorated sputa were that the sputa were more purulent and viscous on gross examination than the induced sputa (Table 3). This could reflect a pooling of secretions overnight in the lower respiratory tract or a dilution of the induced sputa by inhaled saline. Microscopic purulence and salivary contamination were similar in the two groups as well as the isolation rate for the major pathogens (*H. influenzae, M. catarrhalis, S. pneumoniae*; Table 3). These results further demonstrate that spontaneously expectorated sputa in patients with COPD are comparable to induced sputa and can be used to study the lower respiratory tract milieu.

TABLE 3

Comparison of induced and spontaneous sputa

| Characteristic | Spontaneous mean value (range) | Induced mean value (range) | P value |
|---|---|---|---|
| Weight (mg) | 7.84 (1–35) | 6.94 (1–28) | ns |
| Purulence score | 2.33 (1–3) | 2.00 (1–3) | 0.016 |
| Viscosity score | 1.80 (1–3) | 1.59 (1–3) | 0.02 |
| Non-squamous cells/lpf* score | 2.77 (1–3) | 2.69 (1–3) | ns |
| Squamous cells/lpf score | 1.94 (1–3) | 1.79 (1–3) | ns |
| % NTHI isolated | 28.8% | 25% | ns |
| % *M. catarrhalis* isolated | 15.4% | 15.4% | ns |

TABLE 3-continued

Comparison of induced and spontaneous sputa

| Characteristic | Spontaneous mean value (range) | Induced mean value (range) | P value |
|---|---|---|---|
| % S. pneumoniae isolated | 9.6% | 7.5% | ns |
| Sputum fibrinogen level mean (± 1 SD) | 4,400 (±4,100) | 3,600 (±4000) | ns |

*Low power field (10x) of microscope

EXAMPLE 3

This embodiment describes the measurement of inflammation markers in sputum samples obtained as described in Examples 1 and 2. All sputum supernatants and standards were tested in duplicate and mean values were used. Intra-assay coefficient of variation of <10% and inter-assay coefficient of variation of <15% were accepted. Because of limited volume of sputum supernatant available for a small number of samples, all measurements were not performed on all samples. The following assays were performed.

IL-8 Assay

A sandwich enzyme linked immunosorbent assay (ELISA) assay was developed. Commercially available reagents were used for this assay (e.g., from R&D Systems, Minneapolis, Minn.). All intermediate washes were done with plate wash buffer (PWB, PBS with 0.05% Tween-20). Standard microtiter wells were coated with 50 µl of goat anti-human IL-8 antibody diluted to 4 µg/ml in CBC buffer (0.1M sodium carbonate, 0.1M sodium bicarbonate, pH 9.6) overnight at room temperature. The coating antibody was aspirated and the wells blocked with 300 µl of 3% nonfat dried milk in PWB for 1 hr. The wells were washed, dried and then coated with a buffer solution (such as 50 µl of Stabilcoat™, Surmodics, Minn.) for 45 minutes. After removing the Stabilcoat, the plates were dried overnight at room temperature and used for detection of IL-8 activity or stored at 4° C. for use at a later time.

Serial dilutions of recombinant IL-8 and 1:10 dilution of sputum supernatants in 1% nonfat dried milk in PWB were prepared. Fifty µl of the standard or sample was added to the wells and incubated at 37° C. for 2 hr. After washing, 50 µl of biotinylated anti-human IL-8 diluted to 200 ng/ml in 1% nonfat dried milk in PWB was added to the wells for 1 hr at 37° C. After washing, bound biotinylated antibody was detected with streptavidin-horseradish-peroxidase and the optical density of the wells was read at 450 nm. A standard curve was generated from the wells containing recombinant IL-8 and the amount of IL-8 in the samples was read from this curve. The lower limit of detection of IL-8 in this assay was 5 pg/ml and the linear range was 20 pg/ml to 12,500 pg/ml.

TNFα Assay

A sandwich ELISA similar to the IL-8 ELISA was developed with commercially available reagents (R&D Systems). Homogenized sputum supernatants were tested without further dilution. The lower limit of detection of TNFα was 10 pg/ml and the linear range was 80 pg/ml to 5,000 pg/ml.

NE Assay

Elastase activity in undiluted sputum supernatants was determined with a calorimetric assay with a synthetic substrate; N-methoxysuccinyl-ala-ala-pro-val p-nitroanilide, as described previously. A standard curve was generated by titrating commercially available enzyme (Elastin products, Owensville, Mo.). The lyophilized standard was re-suspended in a 50% glycerol and 50% 0.02 M sodium acetate pH 5.0 solution and serially diluted in PBS from 6.4 to 0.041 units/ml. The substrate solution was prepared by dissolving it in 0.1 HEPES buffer, 0.5 M NaCl, 10% DMSO pH 7.5 to a final concentration of 0.2 mM. One hundred microliters of the substrate solution was added to 50 ul of the standard or sample and incubated at 37° C. for 60 minutes. The resulting solution is then read at 405–570 nm. The minimum elastase activity detectable was 41 mU/ml and the linear range was 94 mU/ml to 3200 mU/ml.

Data Analysis

Non-parametric statistical methods were used for all data with Statview 5.0 software. For unpaired data, the Kruskall-Wallis and Mann-Whitney U rank tests and for paired data, the Wilcoxon signed-rank test was used. Correlation was tested with the Spearman coefficient. A p-value of <0.05 was considered significant.

EXAMPLE 4

This example describes the results of the assays of Example 3. The 81 sputum samples studied were divided into 4 groups: HI (*H. influenzae* isolated as sole pathogen on culture, n=20), HP (*H. parainfluenzae* isolated as sole pathogen on culture, n=27), MC (*M. catarrhalis* isolated as sole pathogen on culture, n=14), and NG (only normal flora isolated on culture, n=20).

Figure 2A:
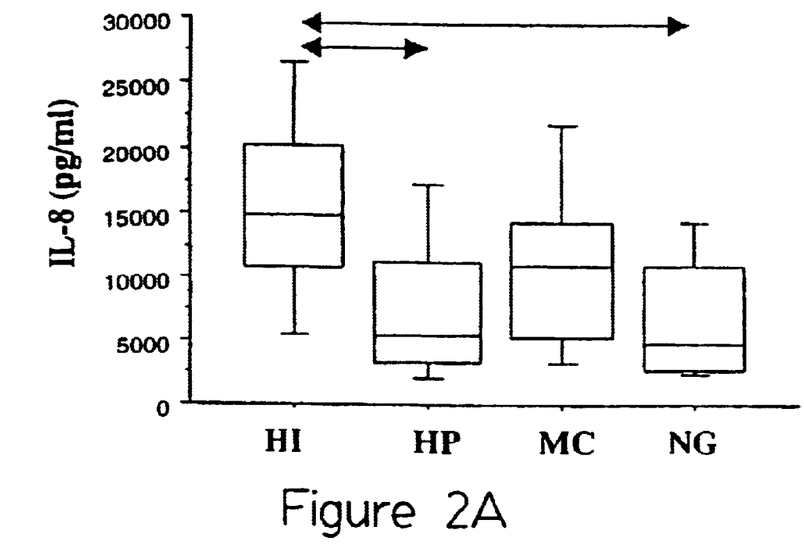
FIGS. 2A–2C are representations of box plots of sputum inflammation in the unpaired groups. The vertical bar represents $10^{th}$ and $90^{th}$ percentile values, the box encompasses the $25^{th}$–$75^{th}$ inter-quartile range and the horizontal line in the box represent median values. The arrows represent significant ($p<0.05$) differences by the Mann-Whitney U rank test. HI=$H.$ $influenzae$ isolated as the sole pathogen on culture, HP=$H.$ $parainfluenzae$ isolated as the sole pathogen on culture, MC=$M.$ $catarrhalis$ isolated as the sole pathogen on culture, NG=only normal flora isolated on culture for Interleukin 8 (IL-8.
Figure 2B:
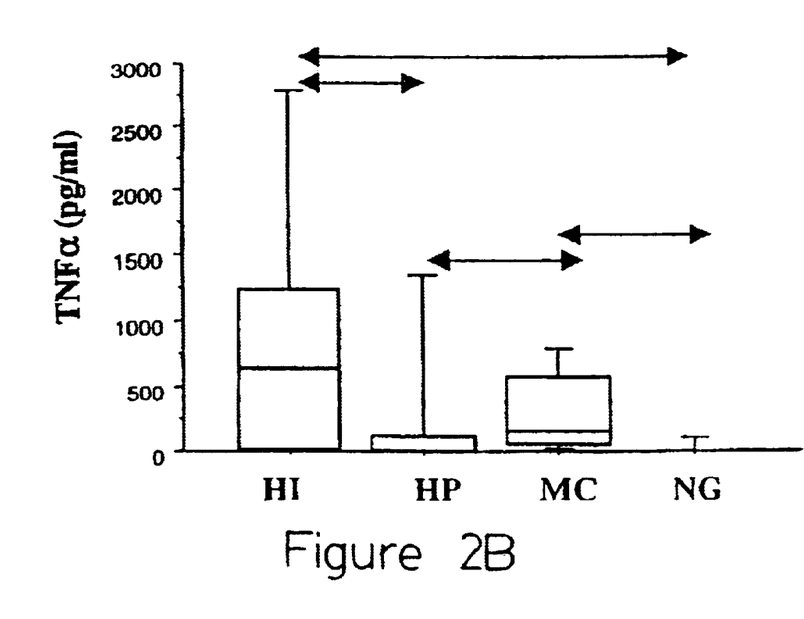
Figure 2C:
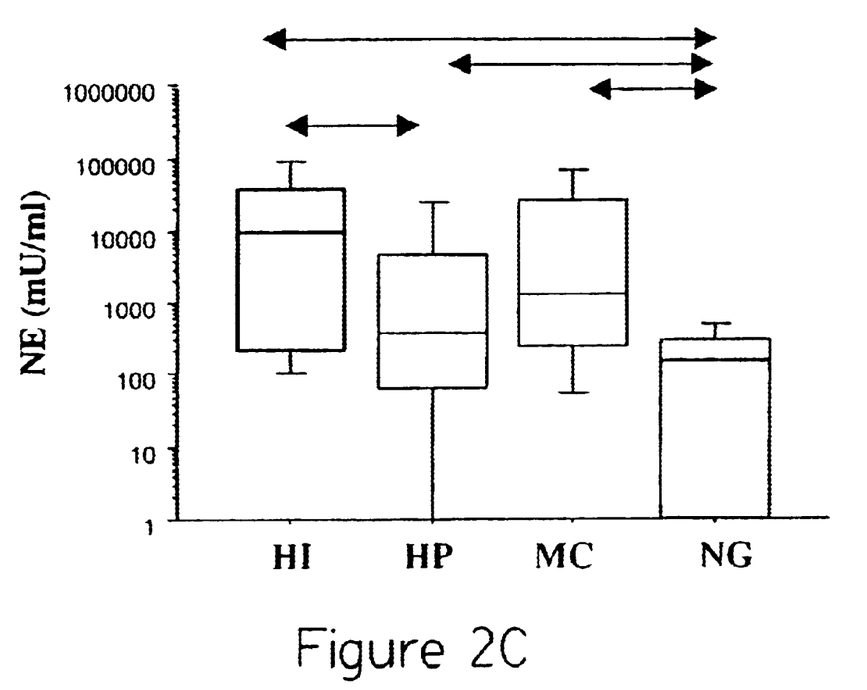

IL-8 was detectable in all 81 sputa tested, TNFα in 40 of the 79 sputa tested and free NE activity in 66 of the 80 sputa tested. FIGS. 2A–2C depict the results obtained. HI exacerbations were associated with significantly higher sputum IL-8, TNFα and NE when compared to pathogen-negative (NG) exacerbations. MC exacerbations were associated with significantly higher sputum TNFα and NE when compared to pathogen-negative (NG) exacerbations. Except for significantly higher sputum NE, airway inflammation in HP exacerbations was similar to pathogen-negative (NG) exacerbations. There were differences in the intensity and nature of inflammation among the different pathogens. HI exacerbations were associated with significantly greater sputum IL-8, TNFα and NE while MC exacerbations were associated with significantly greater sputum TNFα and NE when compared to HP exacerbations. The HI and MC groups did not differ in any of the sputum inflammatory parameters.

These results demonstrate that isolation from sputum of *H. influenzae* or *M. catarrhalis* in an AECB is associated with an airway inflammatory profile characteristic of neutrophilic inflammation. In contrast, non-bacterial AECB are not associated with such an inflammatory profile. Airway inflammation in AECB associated with *H. parainfluenzae* is heterogeneous, however, as a group these AECB have an airway inflammatory profile indistinguishable from non-bacterial exacerbations.

There is overlap between groups in the values obtained of the various inflammatory molecules measured, however, 16 of 19 (84.2%) pathogen-negative (NG) sputa have a NE level below 350 mU/ml, while only 10 of 34 (29.4%) HI and MC sputa have a level below this value. In the HP group, 12 of 27 (44.4%) sputa have sputum NE less than 350 mU/ml.

EXAMPLE 5

This example describes the comparison of inflammation markers in sputum within Patients. Sputum samples used in this study were collected on a longitudinal basis with individual patients contributing from 1 to 4 samples. Comparison of sputum inflammation in pairs of samples obtained from individual patients during two exacerbations, which differ only in the presence or absence of pulmonary pathogens was carried out. Such an analysis accounts for the variability among patients in the baseline level of airway inflammation, and the differences seen within a patient should reflect the presence of pathogens in the airways.

All possible pairs of samples available were included in this analysis. In order to obtain at least 10 pairs for analysis, *H. influenzae* (HI) and *M. catarrhalis* (MC) were combined into a single pathogen-positive (PP) group. To further elucidate the role of *H. parainfluenzae* (HP) as a pathogen, it was treated in this analysis, both as a non-pathogen and as a pathogen. Considering HP as a non-pathogen, pathogen-positive (PP) exacerbations were compared with pathogen-negative (NG) alone, HP alone and a combined NG and HP group. Considering HP as a pathogen, HP, HI and MC exacerbations were combined together and compared with NG exacerbations (Table 4).

Figure 3A:
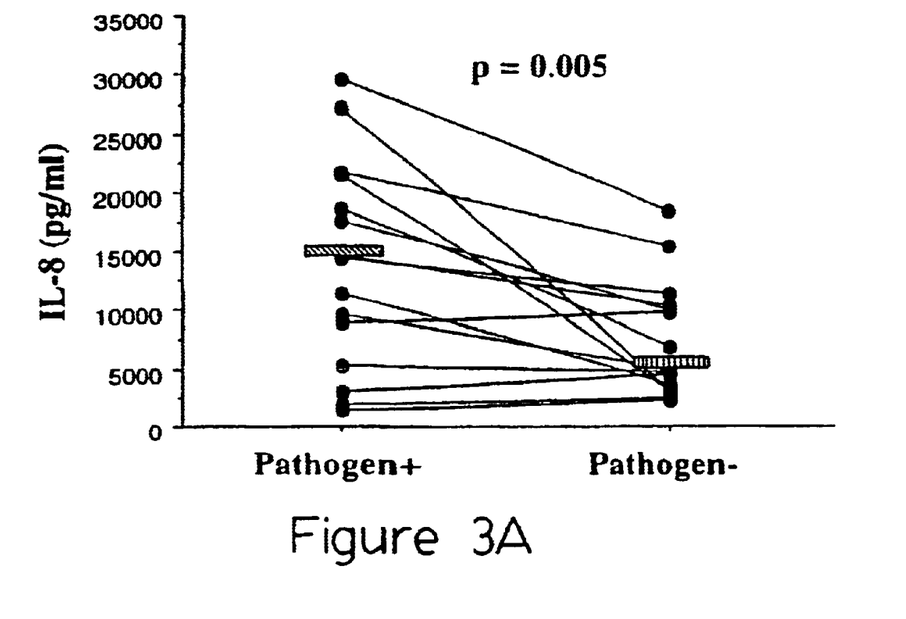
FIGS. 3A–3C are representations of paired comparison of airway inflammation in pathogen-positive AECB (PP) with pathogen-negative AECB (NG). Lines connect the measured values from individual patients. Horizontal bars represent median values. The p-values obtained with the Wilcoxon signed-rank test are shown for Interleukin 8 (IL-8.
Figure 3B:
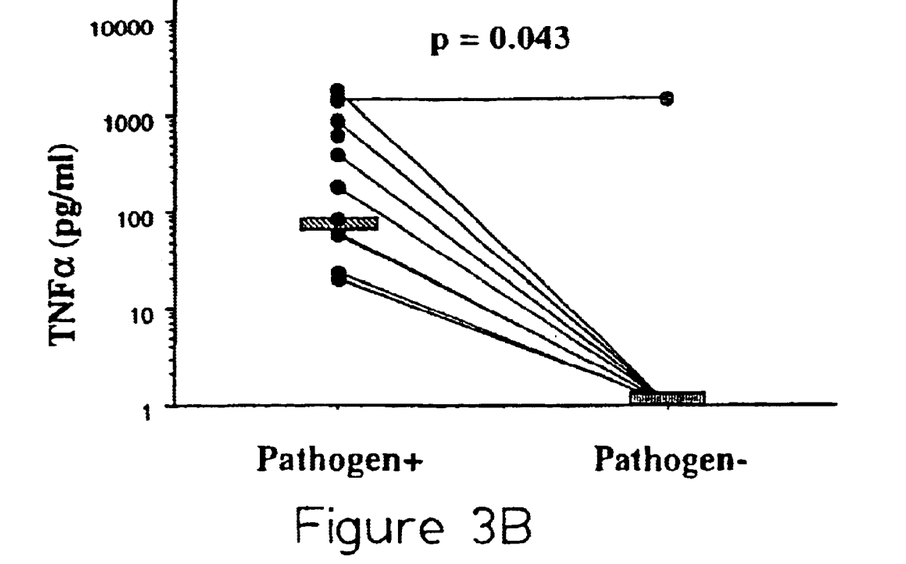
Figure 3C:
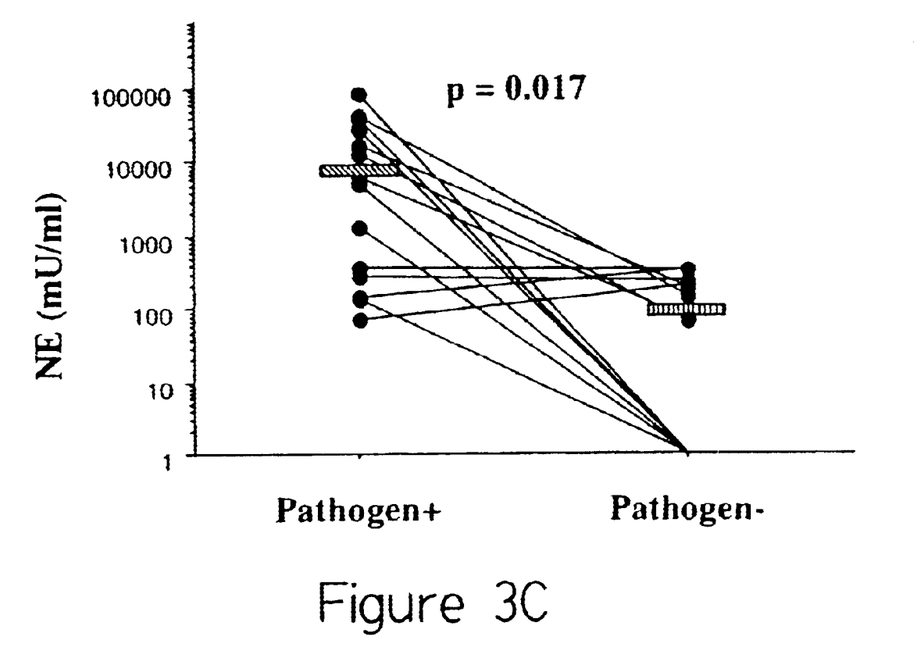

Pathogen-positive AECB were associated with significantly higher sputum IL-8, TNFα and NE than pathogen-negative (NG) AECB (Table 4, FIG. 3). Compared to *H. parainfluenzae* exaerbations, sputum IL-8, TNF-α, and NE were significantly increased in pathogen-positive AECB. *H. parainfluenzae* exacerbations did not differ in any of the sputum inflammatory parameters from the pathogen-negative AECB (Table 4).

Table 4. Comparison of sputum inflammation in paired samples. Median difference is the median of the differences between the first and second values of the pair of samples. Only significant p values obtained with the Wilcoxon signed rank test are shown.

TABLE 4

Comparison of sputum inflammation in paired samples. Median difference is the median of the differences between the first and second values of each pair of samples. Only significant p values obtained with the Wilcoxon signed rank test are shown.

| Sputum culture pairs[a] | Number of pairs | IL-8 (pg/ml) Median difference | TNFa (pg/ml) Median difference | NE (mU/ml) Median difference |
|---|---|---|---|---|
| PP – NG | 12 | 7030 (p = 0.004) | 41 (p = 0.036) | 13152 (p = 0.004) |
| PP + HP – NG | 18 | 4480 (p = 0.012) | 24 (p = 0.012) | 5628 (p = 0.002) |
| PP – HP | 16 | 8350 (p = 0.013) | 57 | 103 |
| PP – NG + HP | 28 | 7830 (p < 0.001) | 44 (p = 0.006) | 1358 (p = 0.002) |

[a]PP = *H. influenzae* or *H. catarrhalis* isolated as the sole pathogen on culture, HP = *H. parainfluenzae* isolated as the sole pathogen on culture, NG = Only normal flora isolated on culture, IL-8 = Interleukin 8, TNFα = Tumor necrosis factor a, NE = Neutrophil elastase.

These results confirm those obtained above with the sputum samples grouped by culture results. They show that within a patient, a bacterial (*H. influenzae* and *M. catarrhalis*) AECB is associated with significantly greater neutrophilic airway inflammation than a non-bacterial AECB. Airway inflammation in AECB associated with *H. parainfluenzae* is heterogeneous; however, within a patient they resemble pathogen-negative AECB.

EXAMPLE 6

Figure 4:
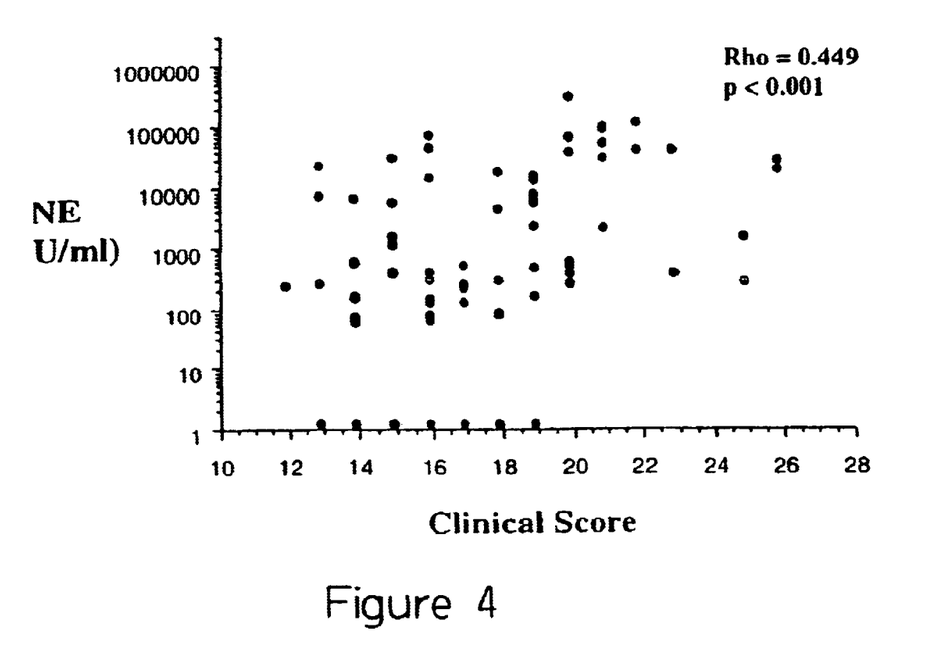
FIG. 4 is a representation of the correlation of free sputum elastase activity (NE) with the clinical score obtained during each exacerbation. Free sputum elastase activity is expressed on the y-axis and the clinical score is expressed on the x-axis. The Spearman correlation coefficient (Rho) and the corresponding p value are also shown.

This example demonstrates a correlation between symptoms for all exacerbations and sputum NE. Clinical scores for the exacerbations included in this study ranged from 12 to 26 with a mean score of 17.5. There was no difference in clinical score among the groups of exacerbations defined by culture results (Kruskall-Wallis, p=ns). There was a significant correlation between clinical score with sputum NE (Rho=0.449, p<0.001; FIG. 4). This corelation was unaffected by exclusion of the 4 outliers with clinical scores >24. However, none of the other inflammatory markers measured showed such a relationship. This observation demonstrates that sputum elastase is a marker of the clinical severity of an AECB and could reflect a cause-effect relationship between the two parameters.

EXAMPLE 7

This example demonstrates a correlation among the inflammatory markers and with bacterial titers in sputum All the three inflammatory markers measured in the sputum demonstrated significant correlation with each other with Rho values of 0.504 for IL-8 and TNFα (p=0.001), 0.396 for IL-8 and NE (p<0.001) and 0.571 for TNFα and NE (p<0.001).

Bacterial titers/gram of sputum (Mean±1 SEM) of HI ($4.89 \pm 1.03 \times 10^8$) and MC ($4.71 \pm 1.13 \times 10^8$) did not differ from each other but were significantly greater than HP ($4.35 \pm 3.69 \times 10^7$) with a p value <0.001 for both comparisons. There was significant correlation between bacterial titres and sputum IL-8 (Rho=0.382, p=0.003), TNFα (Rho=0.437, p=0.001) and NE (Rho=0.381, p=0.003). While not intending to be bound by any particular theory, these results suggest that bacterial infection may be acting as an inflammatory stimulus and as the stimulus increases, there is a corresponding increase in the airway inflammatory response.

The present invention demonstrates that clinical features alone cannot readily distinguish bacterial from non-bacterial AECB. Sputum purulence has often been described as a marker for bacterial exacerbations; but sputum was mucoid on gross examination in only 3 of the 64 exacerbations included in this study. On the other hand, a sputum elastase (NE) level of 350 mU/ml had a sensitivity of 70.6%, specificity of 84.2%, positive predictive value of 88.9% and negative predictive value of 61.5% in distinguishing bacterial (HI or MC) from non-bacterial (NG) AECB. Based on these observations, the present invention provides a semi-quantitative or quantitative method of measuring free sputum elastase for use in clinical practice to distinguish bacterial from non-bacterial AECB. Such measurements would be extremely useful in identifying patients who would benefit from antibiotics.

The foregoing description of the specific embodiments is for the purpose of illustration and is not to be construed as restrictive. From the teachings of the present invention, those skilled in the art will recognize that the device may be modified without departing from the spirit of the invention.

What is claimed is:

1. A method for diagnosis of bacterial exacerbations of chronic lung disease in an individual comprising the steps of:
   a) obtaining a sputum sample from the individual, wherein the sputum sample comprises lower respiratory tract secretions;
   b) determining the level of elastase in the sputum sample by contacting the sputum sample with a chromogenic substrate of elastase; and
   c) comparing the level of elastase in the sputum sample to a reference standard, wherein an increase in the elastase level over the reference standard is indicative of bacterial induced exacerbations of chronic lung disease.

2. The method of claim 1, wherein the chromogenic substrate for elastase activity is N-methoxysuccinyl-ala-ala-pro-val p-nitroanilide.

3. The method of claim 1, wherein the bacterial exacerbation is induced by bacteria selected from the group consisting of $H.$ influenzae, $M.$ catarrhalis, $P.$ aeruginosa and $S.$ pnecumoniae.

4. The method of claim 3, wherein the bacteria is $H.$ influenzae.

5. The method of claim 3, wherein the bacteria is $M.$ catarrhalis.

6. The method of claim 3, wherein the bacteria is $S.$ pneumoniae.

7. The method of claim 3, wherein the bacteria is $P.$ aeruginosa.

8. The method of claim 1, wherein the chronic lung disease is chronic bronchitis.

9. The method of claim 1, wherein the sputum sample is processed to remove cellular components prior to determination of elastase levels.

10. A method for diagnosis of bacterial exacerbations of chronic lung disease in an individual comprising the steps of:
    a) obtaining a sputum sample from the individual, wherein the sputum sample comprises lower respiratory tract secretions; and
    b) determining the presence or absence of elastase in the sputum sample by contacting the sample with an absorbent carrier coated with a chromogenic substrate therefor, wherein a change in color of the absorbent carrier is indicative of bacterial induced exacerbations of chronic lung disease.

11. The method of claim 10, wherein the chromogenic substrate for elastase activity is N-methoxysuccinyl-ala-ala-pro-val p-nitroanilide.

12. The method of claim 10, wherein the bacterial exacerbation is induced by bacteria selected from the group consisting of $H.$ influenzae, $M.$ catarrhalis, $P.$ aeruginosa and $S.$ pneumoniae.

13. The method of claim 12, wherein the bacteria is $H.$ influenzae.

14. The method of claim 12, wherein the bacteria is $M.$ catarrhalis.

15. The method of claim 12, wherein the bacteria is $P.$ aeruginosa.

16. The method of claim 12, wherein the bacteria is $S.$ pneumonia.

17. The method of claim 10, wherein the sputum sample is processed to remove cellular components prior to determination of presence or absence of elastase.

18. A method for diagnosis of $H.$ Influenzae induced exacerbations of chronic lung disease in an individual comprising the steps of:
    a) obtaining a sputum sample from the individual, wherein the sputum sample comprises lower respiratory tract secretions;
    b) determining the level of IL-8 in the sputum sample; and
    c) comparing the level of IL-8 in the sputum to a reference standard, wherein an increase in the IL-8 over reference standard is indicative of $H.$ influenzae induced exacerbations of chronic lung disease.

19. A method for diagnosis of $H.$ influenzae or $M.$ catarrhalis induced exacerbations of chronic lung disease in an individual comprising the steps of:
    a) obtaining a sputum sample from the individual, wherein the sputum sample comprises lower respiratory tract secretions;
    b) determining the level of TNF-$\alpha$ in the sputum sample; and
    c) comparing the level of TNF-$\alpha$ in the sputum to a reference standard, wherein an increase in the TNF-$\alpha$ over the reference standard is indicative of $H.$ influenzae or $M.$ catarrhalis induced exacerbations of chronic lung disease.

* * * * *

```
SEQUENCE LISTING

<160> NUMBER OF SEQ ID NOS: 1

<210> SEQ ID NO 1
<211> LENGTH: 4
<212> TYPE: PRT
<213> ORGANISM: artificial sequence
<220> FEATURE:
<223> OTHER INFORMATION: part of synthetic substrate for elastase

<400> SEQUENCE: 1

Ala Ala Pro Val
```